(12) United States Patent
Qin et al.

(10) Patent No.: US 10,716,769 B2
(45) Date of Patent: *Jul. 21, 2020

(54) METHOD FOR PREVENTING OR TREATING VIRAL INFECTION AND TUMOR

(71) Applicant: GUANGZHOU JTREAT BIOSCI. LTD., Guangzhou (CN)

(72) Inventors: Weihua Qin, Guangzhou (CN); Guangyu Jiang, Guangzhou (CN)

(73) Assignee: GUANGZHOU JTREAT BIOSCI. LTD., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/351,262

(22) Filed: Mar. 12, 2019

(65) Prior Publication Data

US 2019/0209490 A1 Jul. 11, 2019

Related U.S. Application Data

(60) Division of application No. 15/721,662, filed on Sep. 29, 2017, now abandoned, which is a continuation of application No. PCT/CN2016/078411, filed on Apr. 2, 2016.

(30) Foreign Application Priority Data

Apr. 2, 2015 (CN) .......................... 2015 1 0154291

(51) Int. Cl.
*A61K 31/12* (2006.01)
*A61K 31/05* (2006.01)
*A61P 31/20* (2006.01)
*A61P 31/12* (2006.01)

(52) U.S. Cl.
CPC .............. *A61K 31/12* (2013.01); *A61K 31/05* (2013.01); *A61P 31/12* (2018.01); *A61P 31/20* (2018.01); *C12N 2710/20063* (2013.01); *C12N 2740/16061* (2013.01)

(58) Field of Classification Search
CPC ... A61K 31/05; A61K 31/12; A61P 31/12–22; C12N 2710/20063; C12N 2740/16061
See application file for complete search history.

(56) References Cited

U.S. PATENT DOCUMENTS

| 6,583,149 | B1 | 6/2003 | Giles et al. |
| 2002/0136700 | A1* | 9/2002 | Margosiak ............... A61K 8/34 424/70.21 |
| 2004/0259835 | A1 | 12/2004 | Schnittker et al. |
| 2007/0149618 | A1 | 6/2007 | Cuevas Sanchez et al. |
| 2013/0085133 | A1 | 4/2013 | Severson et al. |

FOREIGN PATENT DOCUMENTS

| CN | 1604782 A | 4/2005 |
| CN | 1234353 C | 1/2006 |
| CN | 101889992 B | 4/2012 |
| EP | 0315964 A1 | 5/1989 |
| JP | 2003-510271 A | 3/2003 |
| WO | WO-9707790 A1 * | 3/1997 ............. A61K 31/10 |

OTHER PUBLICATIONS

Tanaka et al., "Single nucleotide polymorphisms of estrogen receptor in human renal cell carcinoma", Biochemical and Biophysical Research Communications, 2002, pp. 1200-1206, vol. 296.
Chung et al., Prevention and treatment of cervical cancer in mice using estrogen receptor antagonists, PNAS, Nov. 17, 2009, pp. 19467-19472, vol. 106, No. 46.
Steven D. Young, "Inhibition of HIV-1 integrase by small molecules: the potential for a new class of AIDS chemotherapeutics", Current Opinion in Drug Discovery & Development, Jul. 1, 2001, pp. 402-410, vol. 4, No. 4.
Lovheim et al., "Herpes simplex infection and the risk of Alzheimer's disease: A nested case-control study," Alzheimer's & Dementia, 2015, pp. 587-592, vol. 11.
Chen et al., "Relationship between Human Papilloma Virus and Cervical Erosion Carcinogenesis," Journal of Cancer Prevention and Treatment, Aug. 2001, pp. 342-344, vol. 8, no.
Chengkang Xu, "Screening of Cervical Human Papilloma Virus Infection and its Significance," Academic Journal of Sun Yat-sen University of Medical Sciences, 1998, pp. 223-226, vol. 10, No. 3.
Ahn et al., "Effect of Retinoic Acid on HPV Titration and Colposcopic Changes in Korean Patients with Dysplasia of the uterine Cervix," J. Cell Biochem. Suppl., 1997, pp. 133-139, vol. 28, No. 29.
Ahn et al., "Inhibition of HIV-1 Integrase by Galloyl glucoses from Terminalia chebula and Flavonol Glycoside Gallates from Euphorbia pekinensis," Planta Med., May 2002, pp. 457-459, vol. 68, No. 5.
Goldgur et al., "Structuer of the HIV-1 integrase catalytic domain complexed with an inhibitor: A platform for antiviral drug design," Proc. Natl. Acad. Sci., Nov. 9, 1999, pp. 13040-13043, vol. 96, No. 23.
Youling Cai et al., Experimental Study on Killing Effect of Chinese Herb (verrucout) on Condyloma Acuminatum Virus (Hpv), Chinese STD/AIDS, Apr. 2002, pp. 108-109, vol, 8, No. 2.

(Continued)

*Primary Examiner* — Kortney L. Klinkel
*Assistant Examiner* — William Y Lee
(74) *Attorney, Agent, or Firm* — IM IP Law; Chai Im; C. Andrew Im

(57) ABSTRACT

A method for preventing and treating viral infection and tumor using a drug composition having a benzophenone compound and analogues thereof having a symmetrical core structure and having same or different number of hydroxyl substitutions in benzene rings. The drug preparation for preventing and treating HIV, herpes virus and papillomavirus infection and the diseases induced thereby, wherein such viral infections include AIDS, genital warts, flat warts, common warts, herpes simplex, herpes zoster, vaginitis, cervicitis, cervical erosion and senile dementia, as well as cervical cancer, lung cancer, gastric cancer and colon cancer induced thereby. Preparation of hydroxy-substituted benzophenones and analogues thereof together with various compatible excipients into different medicaments or personal disinfected sanitary articles.

6 Claims, No Drawings

(56) References Cited

OTHER PUBLICATIONS

Wu et al., Nucleic Acid real-time fluorescence quantitative PCR detection of 'Huantoujing' lotion on human papillae in vitro, experimental study on tumor virus virus clearance, Practical Application of Integrated Chinese and Western Medicine in Clinics, Apr. 2003, vol. 3, No. 2.
Lovheim et al., "Reactivated herpes simplex infection increases the risk of Alzheimer's disease," Alzheimer's & Dementia, 2015, pp. 593-599, vol. 11.
Wade et al., "Natural-product anti-cancer drug discovery from anti-malarials," Poster Presentations/European Journal of Integrative Medicine 4S, 2012, pp. 133-134, vol. 124-201, pp. 023.
Ho et al., "Artemisinins: Pharmacological actions beyond anti-malarial," Pharmacology & Therapeutics, 2014, pp. 126-139, vol. 142.
Jain et al., "Comprehensive review on current developments of quinoline-based anticancer agents," Arabian Journal of Chemistry, 2016, pp. 1-27.
Farrukh Afaq, "Natural agents: Cellular and molecular mechanisms of photoprotection," Archives of Biochemistry and Biophysics, 2011, pp. 144-151, vol. 508.
Nakagawa et al., "Metabolism of 2-hydroxy-4-methoxybenzophenone in isolated rat hepatocytes and xenoestrogenic effects of its metabolites on MCF-7 human breast cancer cells", Chemico-Biological Interactions, 2002, pp. 115-128, vol. 139, Elsevier Science Ireland Ltd.
Kaihatsu et al., "Potential Anti-Influenza Virus Agents Based on Coffee Ingredients and Natural Flavonols", Natural Products Chemistry & Research, Feb. 22, 2014, vol. 2, Issue 2, OMICS International.

\* cited by examiner

METHOD FOR PREVENTING OR TREATING VIRAL INFECTION AND TUMOR

RELATED APPLICATIONS

This is a divisional application of U.S. application Ser. No. 15/721,662 filed Sep. 29, 2017, which is a continuation application of the International Application PCT/CN2016/078411 with an international filing date of Apr. 2, 2016, which claims the benefit of the Chinese Patent Application CN201510154291.4 filed Apr. 2, 2015, each of which is incorporated herein by reference in its entirety.

FIELD OF THE INVENTION

The present invention relates to uses of a hydroxy-substituted benzophenone compound having a symmetrical or asymmetric structure in the preparation of antiviral and antitumor drugs, and more particularly relates to uses of one or more hydroxy-substituted benzophenone compounds or analogues thereof as highly effective inhibitors for viruses and tumors in the preparation of drugs resistant against HIV, herpes virus and human papilloma virus and anti-tumor drugs, and preparations thereof.

BACKGROUND OF THE INVENTION

Hydroxy-substituted benzophenones and analogs thereof refer to derivatives having more than one hydroxyl substitutions in the two benzene rings of benzophenone, such as 2,2'-dihydroxybenzophenone, 2,2'3'-trihydroxybenzophenone, 2,4,2',4'-tetrahydroxybenzophenone, 2,3,4-trihydroxybenzophenone, 2,2',3'-trihydroxybenzophenone, 2,3,4,2',3',4'-hexahydroxybenzophenone, 2,3,4,2',4',5-hexahydroxybenzophenone, 2,3,3',4,4',5-hexahydroxybenzophenone and the like. At present, many of these hydroxyl-substituted benzophenones and analogues thereof are used as UV absorbers and several of them are also used for cardiovascular and cerebrovascular drugs, such as exifone (chemical name as 3,4,5,2',3',4'-hexahydroxybenzophenone) developed by Pharmascience in France and put on the market as an intelligent improvement drug in 1988, which has functions of increasing cerebral blood flow, reducing cerebral capillary permeability and improving learning and memory capability.

Human immunodeficiency virus (HIV), human papilloma virus (HPV) and herpes virus (HSV) have characteristics of being integrated into the human cells and long-term retention, but each has different genetic and metabolic characteristics.

HIV-1 is a virus that causes AIDS, and encodes three enzymes: reverse transcriptase (RT), protease (PR) and integrase (IN). These three enzymes are basic enzymes essential for HIV replication and infection. Integrase inhibitor with novel mechanisms of action can improve efficacy and work synergistically with existing anti-AIDS drugs to form a new and effective combination therapy. HIV-1 integrase (IN) is one of the three basic enzymes essential for viral replication. Retroviral DNA is inserted into the host chromosomes under the catalysis of the integrase, so that the virus can be replicated after it is integrated with human chromosomes. The integrase controls the HIV to invade the chromosomes, so the integrase inhibitors can inhibit the HIV from invading the chromosomes of normal cells. This is now believed as a great breakthrough in the field of anti-AIDS drug development. HIV-1 integrase acts at a single active site with two DNA substrates of the virus and host having different conformations, which may limit HIV to generate drug resistance to integrase inhibitors; furthermore, the integrase only exists in viruses, and mammals have no such enzyme, so HIV-1 integrase becomes a promising new target protein for anti-HIV drug design (Curr. Opin. Drug. Discov. Devel. 2001, 4, 402-410). Many HIV-1 integrase inhibitors have been identified, some compounds of which show the activity of selectively inhibiting HIV-1 integrase and blocking viral replication, and the two most influential inhibitors are polyhydroxy aromatic ring compounds containing catechol and aryl β-diketonic acid compounds as recently reported. However, they are significantly different from the hydroxybenzophenone in structures.

Alzheimer's disease is the most common dementia disease. Many studies of Alzheimer's disease in recent years have revealed the relation between the infection of type 1 herpes simplex virus and the individuals suffering from Alzheimer's disease. Most people in their bodies carry herpes simplex virus, and during the initial infection of the bodies, the virus will be extremely active and cause the bodies to generate oral ulcers or lips herpes. Herpes virus is a neurotropic virus, and can enter into the nerve tissues and exist for long terms after infection. It is now believed that the accumulation of beta-pastein plaques is the main cause of Alzheimer's disease and that the lip-herpes virus may play an important role in the formation of such plaques. The researchers have detected DNA of the lips herpes virus in the protein plaques using the precise gene analysis technique of "In-situ Polymerization-Chain Reaction" (IS-PCR), which indicates that the virus may lead to the formation of protein plaques. When cells are cultured in the laboratory, the lips herpes virus contributes to the formation of beta-pastein plaques. The researchers, by using the precise gene analysis technique of "In-situ Polymerase Chain Reaction Amplification" (IS-PCR), have detected DNA of the lips herpes virus in the protein plaques, which indicates that the virus may lead to the formation of protein plaques. In two study reports published in the international magazine Alzheimer's & Dementia on Oct. 22, 2014, the researchers from Umea University in Sweden find that the infection of herpes simplex virus may increase the risk of suffering from the Alzheimer's disease for individuals. The study results the clearly analyze the association of herpes simplex virus infection with suffering the Alzheimer's disease; in the first study which conducts a follow-up study long up to an average of 11.3 years on 3,432 individuals, the researchers reveal that the re-activation of herpes virus can double the risk of suffering from the Alzheimer's disease for individuals; in the second study, the researchers detect the body samples of 360 patients with Alzheimer's disease as donated in Medical Biological Library of Umea University. The result shows that the risk of suffering from Alzheimer's disease will be doubled if individuals carry herpes virus. Finally, the researchers conclude that if we use antiviral drugs to treat herpes virus infection, there is a promise of inhibiting and treating Alzheimer's disease of individuals by using the antiviral drugs, and it is possible to develop a novel therapy for treating Alzheimer's disease.

Human papillomavirus (HPV) is closely related to the induction of a variety of mucocutaneous inflammations and cancers, such as genital warts, flat warts, common warts, cervicitis, cervical erosion, oral cancer, esophageal cancer, gastric cancer, colon cancer, rectal cancer, skin cancer, lung cancer and cervical cancer. Genital warts, flat warts and common warts, which are benign mucocutaneous neoplasm caused by human papillomavirus (HPV), are one of the most common transmissible diseases. Human papillomavirus (HPV) has more than 100 subtypes, in which some high-risk subtypes such as type 16, type 18, type 33, type 52 and type 58 viruses are proved to be able to be integrated into the cervical mucosal cell DNA and unable to be killed by the existing drugs, thereby inducing cervical cancer, oral cancer, esophageal cancer, gastric cancer, colon cancer, rectal cancer and skin cancer. Studies show that high-risk human papillomavirus, as the same as smoking, is an important inducement to lung cancer.

HPV can, through the placenta and childbirth process, lead to a vertical transmission from mother to a child, so as to cause the next generation born with a virus and disable the preventive vaccines to work.

In recent years, study results show that 29.3% of patients with cervical erosion have positive HPV and the chance of normal cervix being positive is only 11.1% (Fuqiang CHEN et. al., Journal of Cancer Prevention and Treatment, 2001, 8 (4) 342-344; Chengkang X U, Academic Journal of Sun Yat-sen University of Medical Sciences, 1998, 19 (3): 223-226). According to reports (Ahn ws et al, J Cell Biochem Suppl, 1997; 28-29: 133-139), the expression rate of the high-risk HPV (human papillomavirus) type 16 and type 18 among the patients with the chronic cervicitis is 69%, the detection rate of the high-risk type HPV16 and HPV18 exhibits an increasing trend with the increase of the degree of cervical erosion, the detection rate of the granular or papillary erosion HPV16 and HPV18 are significantly different as compared with that of the normal cervix. It is detected by PCR that the positive rate of HPV16 and HPV18 in cervical cancer reaches 83.33%, and the high-risk HPV DNA is integrated into the chromosomes of host cells, so as to produce tumor proteins E6 and E7 which inhibit the anti-oncogenes p53 and Rb respectively to help cells to escape from the control of p53 and Rb, so as to cause the cell cycle out of control, and consequently the cells normally in a static state actively proliferates and tumors grow. If HPV type 16 and type 18 persist, cytopathic effects of the cervix can be progressed. Cervical HPV infection is different from vulvar infection, since in convex, HPV type 16/18 as a main role commonly causes no warts change, but exists as a recessive infection in a long term, which firstly causes atypical hyperplasia and then cancers while other factors are involved in. Currently, there is relatively a lack of effective drugs for treating genital warts and cervical erosion, because some drugs such as podophyllotoxin d have the problem of being very irritating and generating great toxic side effects, despite the advantage of short treatment course. Specific symptoms thereof are pain, edema, erosion and so on. Recombinant human interferon α-2β gel as an external drug for treating genital warts is commonly recognized an effective drug currently. But these drugs cannot eradicate the virus integrated into the human cells, so the infection lasts for a long time and is unhealed, and finally transforms into a malignant tumor.

Malignant tumors are a serious threat to human health and life. At present, chemotherapy drugs for the clinical application are relatively very toxic, and have poor effects on solid tumors, and the vast majority of patients receiving chemotherapy eventually died of tumor cell metastasis. Therefore, it is a main task for the tumor chemotherapy study to peruse a drug having low toxicity and capable of inhibiting the tumor growth and metastasis.

People have been developing anti-HIV, HSV and HPV virus infection and anti-tumor new drugs.

3,4,5-trihydroxybenzoic acid and its glucose-derived derivatives have the effect of inhibiting HIV-1 integrase (Kane C J et al., Planta Med 2002 May; 68 (5): 457-9), but its activity is not high.

CN1234353C discloses the use of 3,4,5-trihydroxybenzoic acid for antitumor, in particular anti-hepatocellular carcinoma and cervical cancer. But 3,4,5-trihydroxybenzoic acid is known to be unstable in human environmental conditions.

OBJECTS AND SUMMARY OF THE INVENTION

It is an object of the present invention to find a class of hydroxy-substituted benzophenone compounds having a high antiviral and antitumor activity. Such compounds have an anti-herpes virus, anti-human papillomavirus and anti-HIV activity, and have the HIV-1 integrase inhibitory activity, which can inhibit the viruses integrated into chromosome from breeding and prevent the recurrence of viral infection.

It is another object of the present invention to provide medical use of compounds containing hydroxy-substituted benzophenone.

The anti-HIV design of the present invention is based on the crystal structure and the structure-activity relationship for interaction between the HIV-1 integrase and its inhibitors. The HIV-1 integrase exhibits a catalytic effect in the form of dimer or tetramer (Proc. Natl. Acad. Sci. USA, 1 1999, 13040-13043), but the exact properties of the oligomers are still unknown. Therefore, the present invention starts from hydroybenzoic acid compounds having antiviral activity to prepare hydroxyl-substituted benzophenone compounds by condensation, so as to obtain highly active antiviral agents. The present invention synthesizes hydroxy-substituted benzophenones (as shown in the general formula 1) having different structures by the condensation of the hydroxybenzoic acid as a monomer with benzene with the hydroxyl group substituted or not, and simultaneously tests, in respect of each compound, the HIV-1 integrase inhibitory activity and the activities of being resistant to HSV and HPV and inhibiting the growth of various tumor cells.

The present invention relates to use of the hydroxy-substituted benzophenone compound in the preparation of an antiviral drug or a drug for preventing virus-induced diseases, wherein the hydroxy-substituted benzophenone compound is selected from one or more of the compounds represented by the following general formula (1):

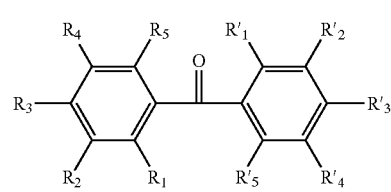

wherein R1, R2, R3, R4, R5 and R'1, R'2, R'3, R'4, R'5 are each independently selected from OH or H, and at least one of R1, R2, R3, R4, R5, R'1, R'2, R'3, R'4 and R'5 is OH.

The virus is HIV, herpes virus or papillomavirus, and the induced diseases are diseases caused by the infection of HIV, herpes virus and papillomavirus, which include tumors that are induced by human papillomavirus.

In the above use, wherein two or more of R1, R2, R3, R4, R5, R'1, R'2, R'3, R'4 and R'5 are OH.

In the above use, wherein two or more of R1, R2, R3, R4, R5, R'1, R'2, R'3, R'4 and R'5 are OH.

In the above use, the hydroxy-substituted benzophenone compound and the analogues thereof can be selected from one of the following compounds: 2,2'-dihydroxybenzophenone, 2,2'3'-trihydroxybenzophenone, 2,3,4-trihydroxybenzophenone, 2,4,2',4'tetrahydroxybenzophenone, 2,3,4,2',3',4'-hexahydroxybenzophenone, 2,3,4,2',4',5-hexahydroxybenzophenone, and 3,4,5,2',3',4'-hexahydroxybenzophenone.

In the above use, the hydroxy-substituted benzophenone compound and the analogues thereof can be selected from one of the following compounds: 2,4,2',4'tetrahydroxybenzophenone, 2,3,4,2',3',4'-hexahydroxybenzophenone, 2,3,4,2',4',5-hexahydroxybenzophenone, and 3,4,5,2',3',4'-hexahydroxybenzophenone.

In the above use, the hydroxy-substituted benzophenone compound and the analogues thereof can be selected from one of the following compounds: 2,3,4,2',3',4'-hexahydroxybenzophenone, 2,3,4,2',4',5-hexahydroxybenzophenone, 3,4,5,2',3',4'-hexahydroxybenzophenone.

In the above use, an effective amount of the aforesaid compound and/or the composition containing the same as an active ingredient are prepared together with various excipients for injections or oral preparations into power injections, water injections, infusions, tablets, capsules, granules or solutions.

In the above use, an effective amount of the aforesaid compound and/or the composition containing the same as an active ingredient are prepared together with various excipients for mucocutaneous preparations into pastes, gels, suppositories, tablets, lotions, films or sprays.

In the above use, an effective amount of the aforesaid compound and/or the composition containing the same as an active ingredient are prepared together with various compatible excipients into the antiviral and antitumor products for spare, wherein the antiviral products are selected from the group consisting of the following personal care products: hand-washing lotions, bathing lotions, hand-washing soaps, bathing sponges, personal care wipers, facial tissues, intranasal sprays, mouthwashes, gynecological vaginal lotions, vaginal lubricants, contraceptives and combinations thereof.

In the above use, it is characterized in that the hydroxy-substituted benzophenone compound is used in drugs for preventing and treating viral diseases and tumors.

In the above use, the viral infection is herpes virus, HIV and human papillomavirus infected by humans and animals.

The above use is the use in the preparation of drugs for preventing and treating mucocutaneous warts.

The above use is the use in the preparation of drugs for preventing and treating herpes virus-induced diseases.

The above use is the use in the preparation of drugs for preventing and treating lips herpes, genital herpes and herpes zoster.

The above use is the use in the preparation of drugs for preventing and treating herpes virus-induced senile dementia, which however, does not include 3,4,5,2',3',4'-hexahydroxybenzophenone.

The above use is the use in the preparation of drugs for removing or reducing the human papillomavirus viral load and preventing viruses from inducing cancers.

The above use is the use in the preparation of drugs for removing or reducing the human papillomavirus viral load and preventing viruses from inducing cervical cancers.

The above use is the use in the preparation of drugs for preventing and treating AIDS.

The above use is the use in the preparation of drugs for preventing and treating tumors.

The above use is the use in the preparation of drugs for preventing and treating cervical cancers.

The above use is the use in the preparation of drugs for preventing and treating gastrointestinal tumors.

The hydroxy-substituted benzophenones represented by the general formula 1 is commercially available or can be prepared by a synthetic reaction as reported in the literature. The synthesis methods of benzophenone includes: (1) benzyl chloride method; (2) benzene and carbon tetrachloride method; (3) benzene and benzoyl chloride method; (4) lead acetate method; (5) phosgene method; and so on.

Various benzoic acids with different numbers of hydroxyl groups (—OH) that are substituted at different positions may be used as the starting materials. The starting materials include but are not limited to p-hydroxybenzoic acid, o-hydroxybenzoic acid, 2,3-dihydroxybenzoic acid, 2,4-dihydroxybenzoic acid, 3,4-dihydroxybenzoic acid, 2,3,4-trihydroxybenzoic acid, 3,4,5-trihydroxybenzoic acid and 2,4,5-trihydroxybenzoic acid. These differently substituted hydroxybenzoic acids are dissolved in a suitable solvent to produce the corresponding hydroxy-substituted benzophenone compound by condensation with benzene with or without hydroxyl substitution under the conditions of the catalyst and heating. The heating can be performed by water bath, oil bath and microwave. The catalyst may be methanesulfonic acid, or a mixture solution of zinc chloride and phosphorus oxychloride.

For example, 2,2',4-trihydroxybenzophenone can be prepared by Friedel-Crafts reaction using salicylic acid and resorcinol as raw materials, anhydrous zinc chloride as a catalyst and chlorobenzene as a solvent.

2,4-dihydroxybenzophenone can be prepared by the reaction of resorcinol aqueous solution and trichlorotoluene.

4,4'-dihydroxybenzophenone can be prepared by Friedel-Crafts reaction using p-hydroxybenzoic acid and phenol as raw materials, and zinc chloride and phosphorus oxychloride as catalysts.

2,3,4,4'-tetrahydroxybenzophenone can be prepared by using pyrogallic acid and p-hydroxybenzoic acid as raw materials.

Test of Inhibition to HIV-1 Integrase

Pharmacological data shows that these hydroxy-substituted benzophenone compounds have a very high HIV-1 integrase inhibitory activity. The half-inhibitory concentration $IC_{50}$ for 3' excision of the substrate and the strand transfer is in the range of 88.92-10.20 μg/ml, in which the best inhibitory activity of the compound is higher than that of the monomer compound of hydroxybenzoic acid. The mechanism of the HIV-1 integrase is a two-step reaction: 1) 3' Processing: the integrase binds to the specific sequences of the long terminal repeat region (LTR) of the proviral DNA to form a stable complex, then the endonucleotides of 3' end of nucleoside is processed, and the GT dinucleotide of the sequence . . . CAGT-3' end is specifically excised, thereby the recessed 3'-hydroxyl is revealed; and 2) Strand Transfer: the processed DNA/integrase pre-integrated complexes pass through the nucleus membrane into the center of the nucleus and bind to the host DNA, then the integrase catalyzes the recessed 3'-hydroxyl of the viral DNA to insert into the chromosome of the host cells by transesterification, and consequently they become mature proviruses. Thus, the activity of the integrase inhibitor is embodied in inhibiting the excision of the 3'end of the viral DNA or the strand transfer, and is represented by a half-inhibitory concentration $IC_{50}$.

In vitro integrase test, 30 synthetic oligonucleotides are used as donor substrates, 20 synthetic oligonucleotides are used as target substrates. Purified HIV-1 integrase is added to donor substrates coated 96-well plate, ELISA reaction is performed, the product of the strand transfer of target DNA is detected, color development is conducted by biotin-labeled alkaline phosphatase system, and the microplate reader is used to measure the OD value.

First, inhibitors of the enzyme may be screened by adding a sample to the reaction system. Before use, the sample is prepared with DMSO to an appropriate concentration, and then is diluted 5 times at 4 dilutions. The sample after dilution is added into the donor substrate coated 96-well plate, and then added to the reaction Buffer containing the genetically engineered target enzyme and the biotin-target substrate, incubated under optimal reaction conditions, and colored by biotin-labeled alkaline phosphatase system, and the OD value for absorbance value at 405 nm is measured.

Test of Anti-Herpes Virus Type I, Type II (HSV-I, II) Inhibition

Vero cells (kidney cells of African green monkey) are used as viral hosts to test the inhibition degree of the samples to the cytopathic effects of Vero cells caused by herpes virus type I and type II.

Test of Inhibition to HPV Virus

The aforesaid compounds and/or compositions containing the same are effective in killing and inhibiting HPV type 6/11 and type 16/18, which can be used for the preparation of drugs for preventing and treating viral infection of HPV, preventing and treating genital warts, flat warts, common warts, vaginitis, cervicitis and cervical erosion, cervical cancer, esophageal cancer and other cancers caused by HPV. The present invention observes the effect of active ingredients and products by the detection of the change in the amount of the HPV virus through the real-time quantitative PCR. Such method has been applied in several publications (Youling C A I, et al., Chinese STD/AIDS, 2002, 8: 2,108; Yuansheng W U, Ruijiang F A N, et al., Practical Application of Integrated Chinese and Western Medicine in Clinics, 2003, 3: 2,1).

The effective amount of the above-mentioned compounds and/or compositions containing the same as the active ingredient can be used in the preparation of drugs for treating human and animal viral diseases, in particular for treating human and animal herpes virus (HSV), AIDS (HIV), human papillomavirus (HPV) and other viral diseases, including but not limited to AIDS, genital warts, flat warts, common warts, herpes simplex, herpes zoster, vaginitis, cervicitis and cervical erosion, cervical cancer, gastric cancer, colon cancer and esophagus cancer as well as herpes zoster, lips herpes, oral ulcers, genital herpes induced by herpes virus and senile dementia; and can, through reducing the high-risk human papillomavirus load, reduce the risk of human papillomavirus-induced cancers, such as cervical cancer, gastric cancer, colon cancer, esophageal cancer and lung cancer, so as to play a role in chemoprevention of cancer Test of Inhibition to Tumor Cell Pharmacological data show that an effective amount of the above compounds and/or the compositions containing the same used as an active ingredient can be used in the preparation of drugs for treating human and animal tumors. The hydroxy-substituted benzophenone compounds have a very high tumor inhibitory activity.

An effective amount of the above compounds and/or compositions containing the same used as an active ingredient have an effect on inhibiting the tumor cells. The present invention detects the inhibitory effect of the hydroxy-substituted benzophenone compounds on the proliferation of the in vitro cultured human tumor cells by the methylthiazolyl tetrazolium method.

Thiazole Salt (MTT) Colorimetric Method

The method is used to detect cell viability. The succinate dehydrogenase in mitochondria of live cell allows the exogenous MTT (2.5-diphenyltetrazolium bromide, also known as thiazole salt) to be reduced to insoluble blue purple crystals and precipitate in cells, but dead cells do not have this function. Particles can be dissolved by dimethyl sulfoxide (DMSO) isopropyl alcohol or 10% acidified SDS (sodium dodecyl sulfate), and a microplate reader is used to measure the OD value at A570 wavelength, which indirectly reflects the number of live cells. The method is used for detection of the cytokines bioactivity, as well as anti-tumor drugs and tumor radiosensitivity and cytotoxicity test, and has the characteristics of being simple, fast, economical, sensitive and accurate and having good reproducibility and no need to use radionuclides. This method has been widely used in screening preclinical anticancer drugs and detecting the drug sensitivity of fresh tumor cells. The method is as below:

(1) The tumor cell suspension prepared by 0.25% of trypsin digestion and adjusted to a cell concentration of $10^5$/ml with RPMI1640 containing 10% fetal calf serum is added to a 96-well plate with 100 μl for each well, cultured 24 hours, and then different dosages of drugs are added with 100 μl/well, for which, the negative control groups, positive control groups and withering wells are set, and 4 parallel wells are set for each group.

(2) They are continually cultured in incubator containing 5% of $CO_2$ at 37° C. for 24 to 48 hours. MTT solution (5 g/L) is added to each well before the termination of the experiment. The OD value at A570 nm is detected by microplate reader. The OD value at A570 of the negative group without the addition of drugs is taken as a control. The cell survival rate and cell inhibition rate of drugs are calculated according to the following formula:

Cell survival rate=(*OD* value of test group/*OD* value of control group)×100%

Cell inhibition rate (%)=(*OD* value of the control group−*OD* value of the test group/(*OD* value of the control group−*OD* value of the blank group)

The logarithm of dose is plotted with cell viability, and the $IC_{50}$ value is calculated by the plotting method.

The description will be made by way of examples, but the protection scope is not only limited to these examples.

DETAILED DESCRIPTION OF THE EMBODIMENTS

The main materials (with contents of higher than 99%) adopted in the present invention and the sources thereof:

3,4,5-trihydroxybenzoic acid and propyl 3,4,5-trihydroxybenzoate purchased from Long Yuan Natural Polyphenol Synthesis Plant of Nanjing; 2,3-dihydroxybenzoic acid and 3,4-dihydroxybenzoic acid purchased Zhong Da Chemical Co., Ltd. of Taizhou City; 2,2'-dihydroxybenzophenone, 2,2'3'-trihydroxybenzophenone, 2,4,2',4'-tetrahydroxybenzophenone, 2,3,4-trihydroxybenzophenone, 2,3,4,2',3',4'-hexahydroxybenzophenone, 2,3,4,2',4',5-hexahydroxybenzophenone and 3,4,5,2',3',4'-hexahydroxybenzophenone purchased from Li Cheng Chemical Co., Ltd. of Shanghai.

Example 1 Preparation of Anti-HPV Microemulsion 20 ml 1,2-propylene glycol, 15 ml Tween 80 and 5 ml are mixed and added with sterilized distilled water to a total volume of 100 ml, so as to obtain an external preparation solution. 10 g 2,4,2',4'-tetrahydroxybenzophenone is added to 50 ml of the external preparation solution, the pH thereof is adjusted to 5.5, and then the solution is added with the external preparation solution to 100 ml, so as to obtain 10% anti-HPV microemulsion of the present invention.

Example 2 Preparation of Anti-HPV 2,3,4,2',4',5-hexahydroxybenzophenone Injection 10 g 2,3,4,2',4',5-hexahydroxybenzophenone, 8.5 g sodium chloride, 10 ml 1,2-propanediol and 80 ml Tween 80 are mixed and added with the sterilized distilled water to be dissolved, then added with the sterilized distilled water to 100 ml, the pH is adjusted to 7.4, and then the solution is filtered, potted and sterilized at 100° C. for 30 mins. Consequently, 2,3,4,2',4',5-hexahydroxybenzophenone injection is obtained.

Example 3 Preparation of 2,3,4,2',4',5-hexahydroxybenzophenone Compound Effervescent Tablets 0.25 g 2,3,4,2',4',5-hexahydroxybenzophenone, 0.01 g polyinoside and 0.45 g tartaric acid are screened separately by 80 mesh sieve, and prepared with anhydrous ethanol into damp mass, and then screened by 12 mesh sieve to obtain wet granules, then the wet granules are dried at 50° C. for use. Besides, 0.65 g sodium bicarbonate and 0.02 g dextrin in addition with the sterilized distilled water are prepared into damp mass, and are screened by 12 mesh sieve to obtain wet granules, then the wet granules are dried at 50° C. These granules are mixed with the above dry granules, and the mixed granules are granulated, added with an appropriated amount of sterilized distilled water, baked for a while, added with 0.01 g PEG6000, uniformly mixed, and finally compressed into tablets.

Example 4 Test of Sample Inhibition to HIV-1 Integrase

The test of sample inhibition to HIV-1 integrase is performed by the Chinese National Drug Screening Center.

I. Test Principle:

30 synthetic oligonucleotides are used as donor substrates, 20 synthetic oligonucleotides are used as target substrates, purified HIV-1 integrase is added to donor substrates coated 96-well plate, ELISA reaction is performed, the product of the strand transfer of target DNA is detected, color development is conducted by biotin-labeled alkaline phosphatase system, and the OD value is measured by a microplate reader. The addition of samples to the reaction system can be used to screen inhibitors for the enzyme.

II. Materials and Method for Test:

1. HIV-1 IN: it is extracted and saved by Chinese National New Drug Screening Center and Institute of Pharmaceutical Biotechnology under Chinese Academy of Medical Sciences.

2. Sample Treatment: 10 samples A1-A10 dissolved into DMSO prior to use are prepared into suitable concentrations, and then diluted 5 times at 4 dilutions. Donor substrate and target substrate are from Shanghai Biochemical Synthesis.

3. Method for Test: the samples after dilution are added into the donor substrate coated 96-well plate, then added to the reaction Buffer containing the genetically engineered target enzyme and the biotin-target substrate, incubated under optimal reaction conditions, and colored by biotin-labeled alkaline phosphatase system, and the OD value for absorbance value at 405 nm is measured.

Test Results:

TABLE 1

Preliminary Screening Report of HIV-1 IN Inhibition Experiment

| Sample No. | Initial Concentration (μg/ml) | $IC_{50}$ (μg/ml) |
|---|---|---|
| 2,2'-dihydroxybenzophenone | 109 | 15.32 |
| 2,2'3'-trihydroxybenzophenone | 109 | 10.46 |
| 2,4,2',4'-tetrahydroxybenzophenone | 109 | 11.23 |
| 2,3,4-trihydroxybenzophenone | 109 | 12.11 |
| 3,4-dihydroxybenzoic acid | 109 | — |
| 2,3-dihydroxybenzoic acid | 109 | — |
| 2,3,4,2',3',4'-hexahydroxybenzophenone | 109 | 9.12 |
| 2,3,4,2',4',5-hexahydroxybenzophenone | 109 | 10.51 |
| 3,4,5-trihydroxybenzoic acid | 109 | 100.46 |

Note:
"—" in the table indicates that the inhibition activity to HIV-1IN for the sample at the initial concentration is less than 50%.

Conclusion: the screening results of the experiment for in vitro drugs inhibition to HIV-1 IN show that the effective concentrations ($IC_{50}$), in which the samples 2,2'-dihydroxybenzophenone, 2,2'3'-trihydroxybenzophenone, 2,4,2',4'-Tetrahydroxybenzophenone, 2,3,4-trihydroxybenzophenone, 2,3,4,2',3',4'-hexahydroxybenzophenone, and 2,3,4,2',4',5-hexahydroxybenzophenone inhibit half of HIV-1IN are 15.32 μg/ml, 10.46 μg/ml, 11.23 μg/ml, 12.11 μg/ml, 9.12 m/ml and 10.51 μg/ml respectively. Other samples have HIV-1IN inhibition activities of $IC_{50}$>109 μg/ml.

Example 5: Test of HPV Detection Via Fluorescence Quantitative PCR for Drugs Screening The microemulsion obtained in example 1 is used as a test sample and saline for blank control.

HPV Virus Source:

The standard clinical genital warts specimens from a variety of patients after being cut off are washed with saline for removing bloods, and are cut into pieces under aseptic conditions, added with saline in 3 times of their volumes to be uniformly mixed, grinded into homogenate and placed at −40° C. for use.

Test Method:

Each test sample drug microemulsion and the saline of 50 μl for each are respectively added with 50 μl the genital warts tissue homogenate, and incubated at 37° C. for 24 hours; tests are performed according to the operation procedure provided by the HPV6, 11 and 16, 18 type FQ-PCR diagnostic kits provided by Da'an Gene Diagnostic Center. 0.2 ml of DNA extracted by the conventional alkaline lysis method is put into the thin-walled reaction tube, and simultaneously added with primers, F-PROBE, DNTP, DNA polymerase, buffers and the like in a certain concentration; ABI PRISM™ 7700 fluorescence quantitative PCR amplifier is used to repeat 40 circulations each with 45 s at 93° C. and 120 s at 55° C. after predegeneration at 93° C. for 2 mins; the quantitative results are automatically analyzed by the computer software to calculate the quantitative results of the initial copy number. The data are shown in Table 2 (completed by Da'an Gene Clinical Test Center).

TABLE 2

Test of HPV Detection via Fluorescence Quantitative PCR for Drugs Screening

| Tube No. | HPV 6/11 Virus (copy/ml) | HPV16/18 (copy/ml) |
|---|---|---|
| Blank Control Tube | $1.458 \times 10^6$ | $1.40 \times 10^5$ |
| 3,4,5-trihydroxybenzoic acid | 0 | 0 |
| Propyl gallate | 0 | 0 |
| 2,2'-dihydroxybenzophenone | 0 | 0 |
| 2,2'3'-trihydroxybenzophenone | 0 | 0 |
| 2,4,2',4' tetrahydroxydiphenylketone | 0 | 0 |
| 2,3,4-trihydroxybenzophenone | 0 | 0 |
| 2,3,4,2',3',4'-hexahydroxybenzophenone | 0 | 0 |
| 2,3,4,2',4',5-hexahydroxybenzophenone | 0 | 0 |
| 3,4-dihydroxybenzoic acid | $1.90 \times 10^4$ | $8.50 \times 10^4$ |
| 2,3-dihydroxybenzoic acid | $2.30 \times 10^4$ | $3.20 \times 10^3$ |

The results show that 24 hours later after the addition of test compounds 2,2'-dihydroxybenzophenone, 2,2'3'-trihydroxybenzophenone, 2,4,2',4'tetrahydroxybenzophenone, 2,3,4-trihydroxybenzophenone, 2,3,4,2',3',4'-hexahydroxybenzophenone and 2,3,4,2',4',5-hexahydroxybenzophenone into the tissue homogenate of genital warts, HPV 6/11 and HPV16/18 virus can no longer be detected by FQ-POVR. The groups of 3,4-dihydroxybenzoic acid and 2,3-dihydroxybenzene, however, have a high concentration HPV6/11 and HPV16/18 virus content, and the blank group also has a high HPV6/11 and HPV16/18 virus content, which shows that the compounds of the present invention have an ability of fast and effectively killing HPV virus in vitro.

Example 6: Test of Inhibition to Anti-Herpes Virus Type I, II (HSV-I, II)

I. Test Principle:

Vero cells (kidney cells of African green monkey) are used as viral hosts to test the inhibition degree of the samples to cytopathic effects of the Vero cell caused by herpes virus type I and type II.

II. Materials and Methods for Test

1. Virus strains: HSV-I, VR733 strain, and HSV-II, SAV strain, which both are provided by ATCC.

2. Sample treatment: the sample is dissolved in DMSO at an appropriate concentration before use, and diluted with the culture medium 3 times at a total of 8 dilutions for test.

3. Positive control drug: acyclovir (ACV) produced by the Hubei Ke Yi pharmaceutical factory.

4. Test method: Vero cells are planted on a 96-well culture plate, and after 24 hours, infected with herpes virus type I $10^{-3}$ (50 times of $TCID_{50}$ infection) and herpes virus type II $10^{-4}$ (10 times of $TCID_{50}$ infection), and absorbed for 2 hours; the virus solution is discarded; the samples and positive control drugs are added according to the above dilution; simultaneously the cell control wells and the virus control wells are set; the cytopathic effects (CPE) are observed for 48 hours; and the half inhibitory concentrations ($IC_{50}$) of the samples against the herpes virus type I and type II are respectively calculated by the Reed-Muench method.

III. Test Results:

TABLE 3

Screening Report of Anti-herpes Virus Type I and II (HSV-I, II) Activity

| Sample No. | $TC_{50}$ (µg/ml) | Against HSV-1 $IC_{50}$ (µg/ml) | SI | Against HSV-II $IC_{50}$ (µg/ml) | SI |
|---|---|---|---|---|---|
| Blank | — | — | — | — | — |
| 2,2'-dihydroxybenzophenone | 64.15 | 28.74 | 2.18 | 28.74 | 2.23 |
| 2,3,4-trihydroxybenzophenone | 53.42 | 28.74 | 2.66 | 28.74 | 1.86 |
| 2,4,2',4' tetrahydroxybenzophenone | 111.11 | 28.74 | 2.22 | 28.74 | 2.11 |
| 2,3,4,2',4',5-hexahydroxybenzophenone | 86.23 | 28.74 | 3.33 | 28.74 | 3.00 |
| 2,3,4,2',3',4'-hexahydroxybenzophenone | 12.35 | 28.74 | 1.26 | 10.85 | 1.14 |
| ACV | >100 | 1.092 | >91.57 | 1.23 | >81.30 |

Note:
(1) "—" in the table indicates there's no anti-herpes virus activity for the samples at the maximum non-toxic dose.
(2) $TC_{50}$: half toxic concentration; $IC_{50}$: half inhibitory concentration to virus; SI: selectivity index, SI = $TC_{50}/IC_{50}$.

The results show that the above mentioned various hydroxy-substituted benzophenones have different inhibitory rates on both HSVI and HSV-II after the addition of the test compounds.

V. Clinical Observation of Treatment of Lips Herpes:

1. Materials:

20 ml glycerol, 20 ml 1,2-propylene glycol, 15 ml Tween 80 and 5 ml are mixed and added with sterilized distilled water to a total volume of 100 ml for obtaining the external preparation solution. 10 g 2,3,4,2',4',5-hexahydroxybenzophenone is added with 50 ml external preparation solution with pH thereof adjusted to 5.5, and then is added with the external preparation solution to 100 ml, for obtaining a anti-HPV microemulsion containing 10% of the compound of the present invention, which is referred to as A; acyclovir ointment sold in pharmacy market (produced by Shanghai General Pharmaceutical Co., Ltd.) is referred to as the B.

2. Methods and Results:

10 patients with lips herpes were randomly divided into group A and group B;

Group A: 5 patients are smeared with A, 4 times a day, and all 5 patients scab at the next day;

Group B: 5 patients are smeared with B, 4 times a day, 2 patients scab at the third day, and 3 patients scab at the fifth day;

The efficacy of group A is significantly better than that of group B;

This shows that 2,3,4,2',4',5-hexahydroxybenzophenone has an anti-herpes function and can be used to treat herpes infection.

Example 7 Test of Compounds Resistant to Tumor In Vitro

I. Materials for Test

1. Tumor cell lines: human glioma cell line (U251), human colon cancer cell line (LOVO), human hepatoma cell line (HepG2), human lung cancer cell line (PC84045), human endometrial carcinoma cell line (JEC), human renal carcinoma (GRC), human gastric cancer cell line (MCG804), human cervical cancer cell line (HeLa), human hepatocellular carcinoma cell line (BEL-7402) and human umbilical vein endothelial cell line (ECV304) purchased from Animal Experimental Center of Zhongshan Medical College, and preserved by the present laboratory.

2. Main instruments and reagents for test: $CO_2$ humidification incubator of Sheldon company; bechtop of Suzhou Purification Equipment Factory; microplate reader of Biored Company; trypsin of Sigma Company; RPMI-1640 medium of Gibco Company; 96-well culture plate of Corning Company; newborn bovine serum of Hangzhou Sijiqing Company.

II. Method for Test

1. Cell Culture:

The tumor cell lines are cultured in RPMI-1640 medium containing 15% of the newborn bovine serum in a conventional manner, placed in the humidification incubator containing 5% of $CO_2$ for being cultured at 37° C., and are observed for growth by an inverted microscope. A subculture is conducted every about 3-5 days, the cells in logarithmic growth phase are adopted to be digested with 0.25% of trypsin, and the serum-free RPMI-1640 medium is used for culturing the cell suspension; the blood counting plate makes counting, the trypan blue exclusion tests the cell activity, and the cell viability>95% is used for formal tests [1].

2. MTT Method

Liquid preparation: the compounds are labeled with the codes respectively, DMSO is used to dissolve each compound, the bacterial filter is used to remove bacteria, and each compound is prepared into $10^{-4}$ g/ml, $10^{-5}$ g/ml, $10^{-6}$ g/ml and preserved at 4° C. for use.

MTT method: a bottle of 4-5 days old cells in the exponential growth phase are adopted to be cultured, and added with an appropriate amount of Trypsin-EDTA solution, so as to enable the adherent cells to fall off, and are prepared with 10 ml of RPMI-1640 medium containing 15% newborn bovine serum into suspensions; after stained with trypan blue, the cell number is counted on the blood counting plate to ensure that the live cells is more than 97%; the cell suspensions are diluted by the complete medium so that each 100 ml of solution contains 5000-400000 cells; the 96-well plate is used with 200 μl of cell suspensions added into each. The 96-well plate is placed at 37° C. in 5% of $CO_2$ containing incubator for 24 hours; the test compounds are diluted at 3 dilutions with 5 wells in parallel for each concentration; the serum-free RPMI1640 is used as the control group. The 96-well plate is incubated in incubators having 5% of $CO_2$ and 100% humidity at 37° C. for 3 days; MTT is prepared to 1 mg/ml solution with serum-free RPMI 1640 medium, and each well is added with 50 μl thereof and incubated at 37° C. for 4 hours, so as to reduce the MTT to formazan; the supernatant is aspirated, 200 μl of DMSO is added to dissolve the formazan and the obtained solution is shaken with a plate shaker for 5 minutes to be uniform; the microplate reader is used to measure the light absorbance value, measures the absorbance value of each well at a wavelength of 570 nm with a reference wavelength of 630 nm; the obtained data is processed by SPSS11.0 statistic software to calculate the inhibitory rate of the cells.

Inhibitory rate %=(1−average absorbance value of sample group/average absorbance value of solvent group)×100%

3. Determination of Results

Inhibitory rate>50% means sensitive;
30%~50% means moderately sensitive;
<30% means insensitive.

III. Test Results and Analysis

TABLE 4

Report of In Vitro Inhibition of Compounds to Tumor Cells

| | Inhibitory rate % | | | | | | | | |
|---|---|---|---|---|---|---|---|---|---|
| | 2,3,4,2',4',5-hexahydroxybenzophenone | | | 2,3,3',4,4',5-hexahydroxybenzophenone | | | 2,3,4,2',3',4'-hexahydroxybenzophenone | | |
| Cell lines | $10^{-4}$ g/ml | $10^{-5}$ g/ml | $10^{-6}$ g/ml | $10^{-4}$ g/ml | $10^{-5}$ g/ml | $10^{-6}$ g/ml | $10^{-4}$ g/ml | $10^{-5}$ g/ml | $10^{-6}$ g/ml |
| U251 | 68.82 (sensitive) | 31.35 (moderately sensitive) | insensitive | 64.27 (sensitive) | insensitive | insensitive | 83.26 (sensitive) | 30.87 (moderately sensitive) | insensitive |
| LOVO | 51.19 (sensitive) | insensitive | insensitive | 75.61 (sensitive) | insensitive | insensitive | insensitive | insensitive | insensitive |
| HepG2 | 85.12 (sensitive) | 51.57 (sensitive) | insensitive | 77.03 (sensitive) | 55.49 (sensitive( | insensitive | 86.15 (sensitive) | 75.54 (sensitive) | insensitive |
| PC84045 | 82.49 (sensitive) | 70.97 (sensitive) | 49.70 (moderately sensitive) | 80.43 (sensitive) | 70.86 (sensitive) | 41.369 (moderately sensitive) | 84.60 (sensitive) | 72.34 (sensitive) | insensitive |
| JEC | 83.16 (sensitive) | 42.57 (moderately sensitive) | insensitive | 79.84 (sensitive) | 32.36 (moderately sensitive) | insensitive | 85.63 (sensitive) | 42.79 (moderately sensitive) | insensitive |
| MCF7 | 73.19 (sensitive) | 35.48 (moderately sensitive) | insensitive | 65.36 (sensitive) | insensitive | insensitive | 76.37 (sensitive) | 43.52 (moderately sensitive) | insensitive |
| MCG804 | 83.48 (sensitive) | 72.89 (sensitive) | insensitive | 71.91 (sensitive) | insensitive | insensitive | 80.93 (sensitive) | 30.12 (moderately sensitive) | insensitive |
| HeLa | 60.92 (sensitive) | insensitive | insensitive | 58.94 (sensitive) | insensitive | insensitive | 61.12 (sensitive) | insensitive | insensitive |
| ECV304 | 72.41 (sensitive) | 53.62 (sensitive) | 30.75 (moderately sensitive) | 70.81 (sensitive) | 43.47 (moderately sensitive) | insensitive | 79.37 (sensitive) | insensitive | insensitive |

TABLE 4-continued

Report of In Vitro Inhibition of Compounds to Tumor Cells

| | Inhibitory rate % | | | | | | | | |
|---|---|---|---|---|---|---|---|---|---|
| | 2,3,4-tridyroxybenzophenone | | | 2,4-dihydroxybenzophenone | | | | | |
| Cell lines | $10^{-4}$ g/ml | $10^{-5}$ g/ml | $10^{-6}$ g/ml | $10^{-4}$ g/ml | $10^{-5}$ g/ml | $10^{-6}$ g/ml | 2,4,2',4'tetrahydroxybenzophenone | | |
| U251 | 85.42 (sensitive) | 43.57 (moderately sensitive) | insensitive | 85.31 (sensitive) | 67.25 (sensitive) | 31.21 (moderately sensitive) | | | |
| LOVO | 90.02 (sensitive) | 46.78 (moderately sensitive) | insensitive | 93.80 (sensitive) | insensitive | insensitive | 53.29 (sensitive) | insensitive | insensitive |
| HepG2 | 93.40 (sensitive) | 58.05 (sensitive) | insensitive | 94.78 (sensitive) | 66.74 (sensitive) | 58.63 (sensitive) | 74.85 (sensitive) | insensitive | insensitive |
| PC84045 | 85.75 (sensitive) | 32.79 (moderately sensitive) | insensitive | 92.65 (sensitive) | 89.88 (sensitive) | 44.39 (moderately sensitive) | 53.40 (sensitive) | insensitive | insensitive |
| JEC | 86.79 (sensitive) | 40.97 (moderately sensitive) | insensitive | 93.58 (sensitive) | 62.30 (sensitive) | 32.56 (moderately sensitive) | 46.70 (moderately sensitive) | insensitive | insensitive |
| MCF7 | 78.59 (sensitive) | 38.60 (moderately sensitive) | insensitive | 87.60 (sensitive) | 68.62 (sensitive) | 28.57 (moderately sensitive) | 45.73 (moderately sensitive) | insensitive | insensitive |
| MCG804 | 87.14 (sensitive) | 62.75 (sensitive) | insensitive | 92.54 (sensitive) | 86.35 (sensitive) | 41.35 (moderately sensitive) | 38.95 (moderately sensitive) | insensitive | insensitive |
| HeLa | 89.81 (sensitive) | 34.53 (moderately sensitive) | insensitive | 95.65 (sensitive) | 48.96 (moderately sensitive) | 37.32 (moderately sensitive) | 31.05 (moderately sensitive) | insensitive | insensitive |
| ECV304 | 89.63 (sensitive) | 45.81 (moderately sensitive) | insensitive | 96.17 (sensitive) | 73.12 (sensitive) | 45.37 (moderately sensitive) | 42.13 (moderately sensitive) | insensitive | insensitive |

The results show that the above-mentioned various hydroxy-substituted benzophenones have different inhibitory rates on various tumor cells after 3 days of addition of the test compounds, and significantly inhibit human lung cancer cell line (PC84045), human endometrial carcinoma cell line (JEC), human renal carcinoma (GRC), human cervical cancer cell line (HeLa), and human hepatocellular carcinoma cell line (BEL-7402). The results demonstrate that the hydroxy-substituted benzophenone compound of the present invention and its analogues are effective in inhibiting tumor cells.

INDUSTRIAL UTILITY

The present invention uses hydroxybenzophenone in the preparation of antiviral and antitumor drugs which can prevent and treat the infection of HIV, herpes virus, papillomavirus and the diseases induced thereby. The hydroxy-substituted benzophenone and its analogues can be prepared together with a variety of compatible excipients into different medicaments or personal disinfected sanitary articles.

What is claimed is:

1. A method for treating human papillomavirus, comprising administering to an individual to be treated a drug composition comprising a hydroxy-substituted benzophenone compound, wherein:
   the hydroxy-substituted benzophenone compound is selected from at least one of compounds represented by the general formulae:

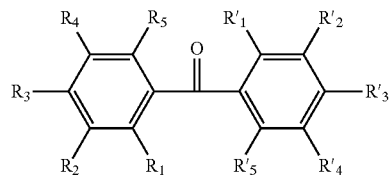

R1, R2, R3, R4, R5 is selected from one of OH and H;
R'1, R'2, R'3, R'4, R'5 is selected from one of OH and H; and
two, three or four of R1, R2, R3, R4, R5, R'1, R'2, R'3, R'4 and R'5 is OH.

2. The method in claim 1, comprising an effective amount of the hydroxy-substituted benzophenone compound as an active ingredient and compatible excipients for formulating mucocutaneous preparations into gels.

3. The method in claim 1, comprising an effective amount of the hydroxy-substituted benzophenone compound as an active ingredient and compatible excipients for formulating a gynecological vaginal lotion.

4. The method in claim 1, wherein the drug composition is administered to the individual for removing or reducing human papillomavirus load from inducing cancers.

5. The method in claim 1, wherein the drug composition is administered to the individual for removing or reducing human papillomavirus load from inducing cervical cancer.

6. The method in claim 1, wherein the hydroxy-substituted benzophenone compound is selected from the group consisting of 2,2'-dihydroxybenzophenone, 2,2'3'- trihydroxybenzophenone, 2,4,2', 4' tetrahydroxydiphenylketone and 2,3,4- trihydroxybenzophenone.

* * * * *